US00PP23035P2

(12) United States Plant Patent
Probst

(10) Patent No.: US PP23,035 P2
(45) Date of Patent: Sep. 11, 2012

(54) ***COREOPSIS* PLANT NAMED 'STAR CLUSTER'**

(50) Latin Name: ***Coreopsis* hybrid**
Varietal Denomination: Star Cluster

(76) Inventor: Darrell R. Probst, Hubbardston, MA (US)

( * ) Notice: Subject to any disclaimer, the term of this patent is extended or adjusted under 35 U.S.C. 154(b) by 30 days.

(21) Appl. No.: 12/932,910

(22) Filed: Mar. 9, 2011

(51) Int. Cl.
*A01H 5/00* (2006.01)

(52) U.S. Cl. ..... Plt./417

(58) Field of Classification Search ..... Plt./417
See application file for complete search history.

*Primary Examiner* — Susan McCormick Ewoldt
(74) *Attorney, Agent, or Firm* — Penny J. Aguirre

(57) ABSTRACT

A new cultivar of hybrid *Coreopsis* named 'Star Cluster' characterized by its large inflorescences with overlapping ray florets that are white in color with small purple eyezones that under cool growing temperatures develop larger eyezones and become suffused with purple first on the petal margins and then in the center of the petals, the ability to bloom from June until frost in Massachusetts, its heavy blooming habit, its well-branched sturdy stems, its vigorous growth habit with healthy foliage, and its reliably perennial habit with cold hardiness at least to U.S.D.A. Zone 5.

2 Drawing Sheets

Botanical classification: *Coreopsis* hybrid.
Variety denomination: 'Star Cluster'.

CROSS REFERENCE TO A RELATED APPLICATION

This application is co-pending with a U.S. Plant Patent Applications filed for plants derived from the same breeding program that is entitled *Coreopsis* Plant Named 'Cosmic Evolution' (U.S. Plant patent application Ser. No. 12/932,911 pending), *Coreopsis* Plant Named 'Cosmic Eye' (U.S. Plant Pat. No. 22,601), and *Coreopsis* Plant Named 'Galaxy' (U.S. Plant Pat. No. 21,999), *Coreopsis* Plant Named 'Redshift' (U.S. Plant Pat. No. 20,412) and *Coreopsis* Plant Named 'Full Moon' (U.S. Plant Pat. No. 19,364).

BACKGROUND OF THE INVENTION

The present invention relates to a new and distinct cultivar of *Coreopsis* plant, botanically of hybrid origin and known as *Coreopsis* 'Star Cluster' and will be referred to hereinafter by its cultivar name, 'Star Cluster'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A Zone 5 in a wide range of flower colors and plant forms. The inventor collected seed in the wild from five different species that are not commercialized and made six generations of crosses to produced interspecific hybrids to utilize in his breeding work.

The Inventor made a controlled cross in summer of 2007 in his test garden in Hubbardston, Mass. between *Coreopsis* 'Redshift' (U.S. Plant Pat. No. 20,412) as the female parent and an unnamed F1 *Coreopsis rosea*×complex hybrid as the male parent. 'Star Cluster' was selected in September 2008 as a single unique plant amongst the resulting seedlings.

Asexual reproduction of the new cultivar was first accomplished by stem cuttings under the direction of the Inventor in Kensington, Conn. in September of 2008. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Star Cluster' as unique from all *Coreopsis* cultivars and species known to the Inventor.

1. 'Star Cluster' exhibits white inflorescences suffused with a small purple eye, under cool growing temperatures the ray florets become suffused with purple first on the petal margins and then in the center of the petals.
2. 'Star Cluster' exhibits over-lapping ray florets.
3. 'Star Cluster' blooms heavily from June until frost in Massachusetts.
4. 'Star Cluster' exhibits well-branched, sturdy stems.
5. 'Star Cluster' exhibits a vigorous growth habit with healthy foliage.
6. 'Star Cluster' exhibits a reliably perennial habit and is cold hardy at least to U.S.D.A. Zone 5.

The female parent differs from 'Star Cluster' in having inflorescences that have a light yellow color base and a more star-shaped outline due to less overlapping of the ray florets. The male parent differs from 'Star Cluster' in having inflorescences that are solid pale yellow in color throughout the season. 'Star Cluster' can be compared to *Coreopsis* cultivars 'Redshift' (U.S. Plant Pat. No. 20,412) and 'Snowberry' (U.S. Plant Pat. No. 18,560). 'Redshift' differs from 'Star Cluster' in having inflorescences that are light yellow in color and a more star-shaped outline due to less overlapping of the ray florets. 'Snowberry' differs from 'Star Cluster' in having inflorescences that are smaller in size and light yellow in color.

BRIEF DESCRIPTION OF THE DRAWING

The accompanying colored photographs illustrate the overall appearance and distinct characteristics of the new *Core-*

*opsis*. The photographs were taken of six month-old plants of 'Star Cluster' as grown in one-gallon containers in Kensington, Conn.

Figure 1:
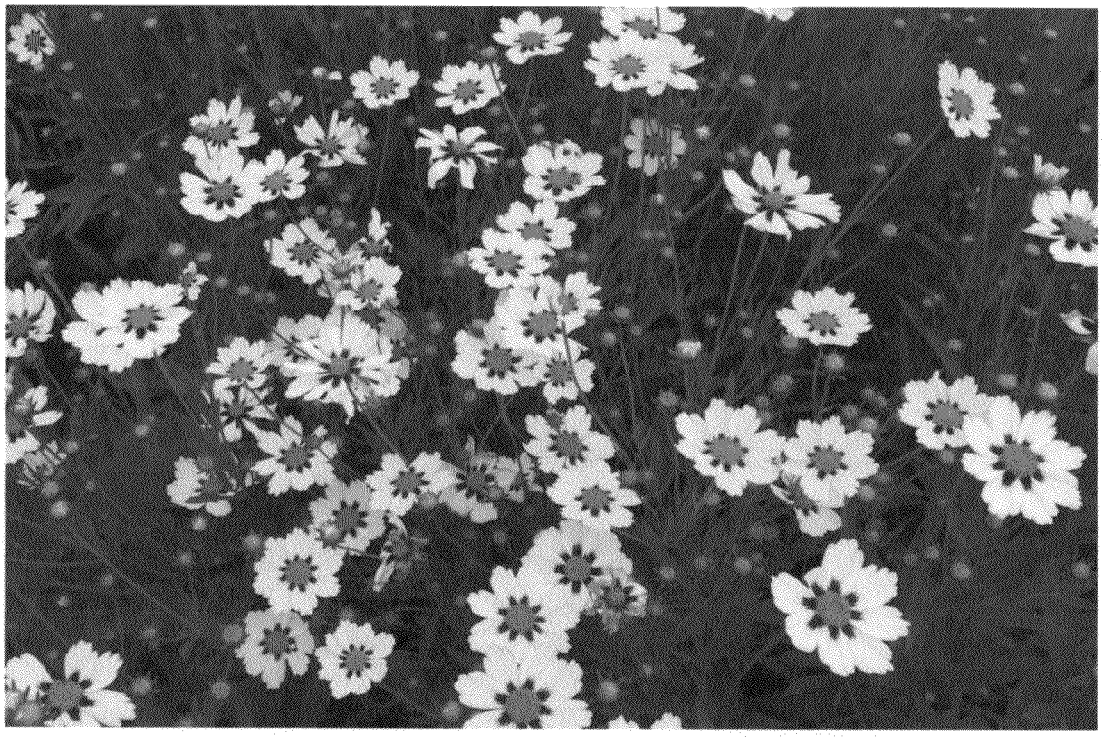

The photograph in FIG. 1 shows a top perspective of 'Star Cluster' in bloom.

Figure 2:
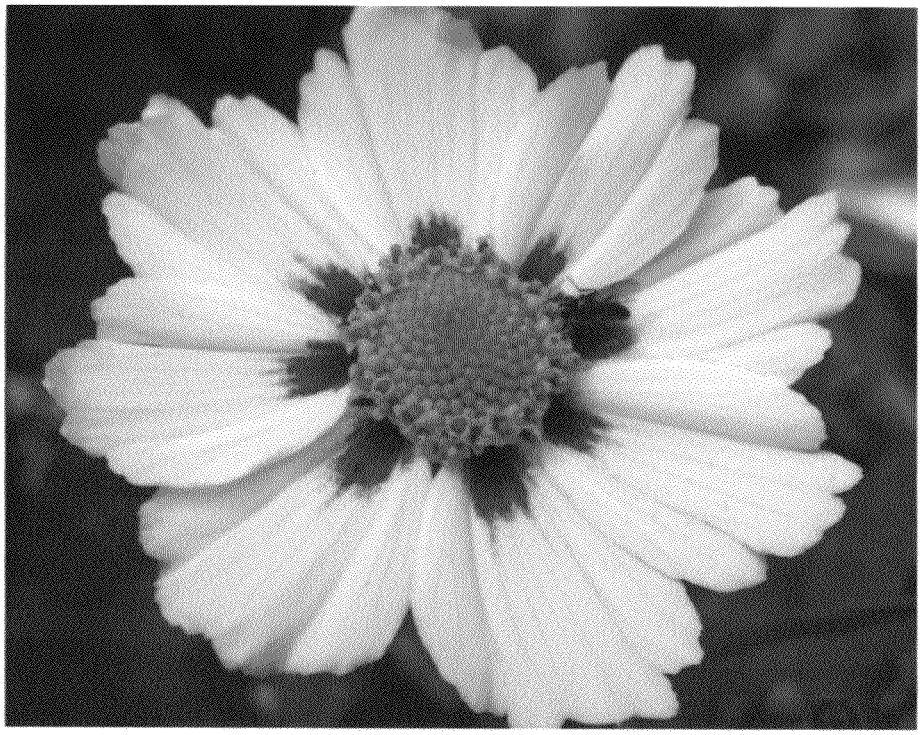

The photograph in FIG. 2 provides a close-up view of an inflorescence of 'Star Cluster'.

Figure 3:
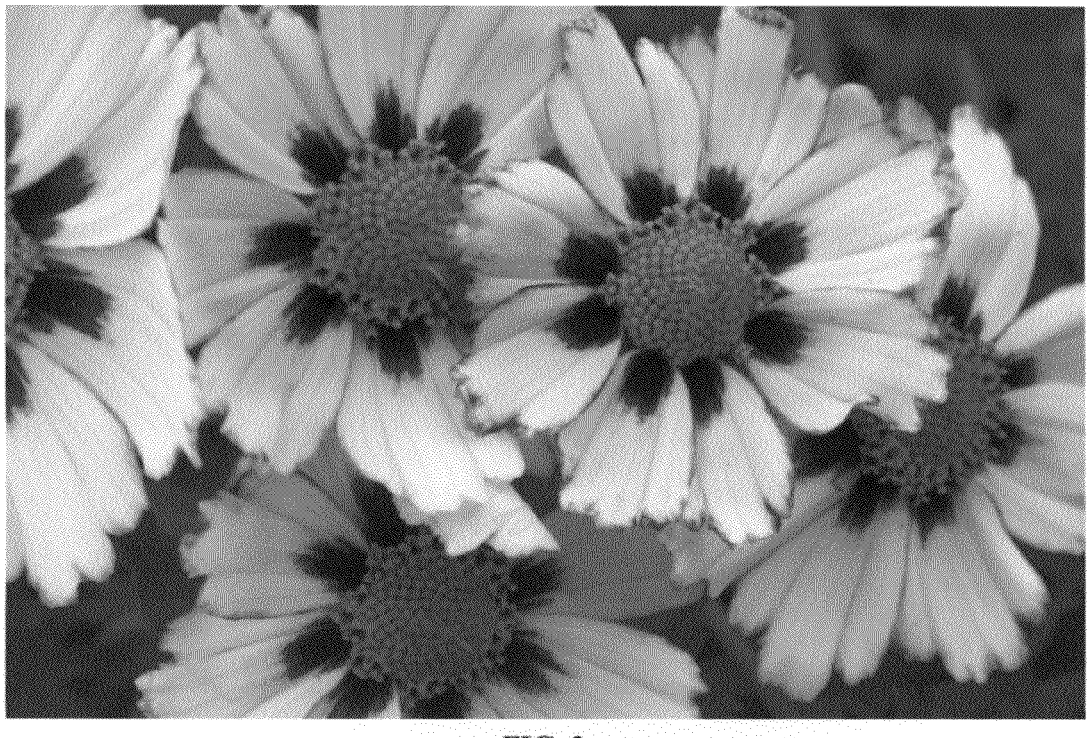
Figure 4:
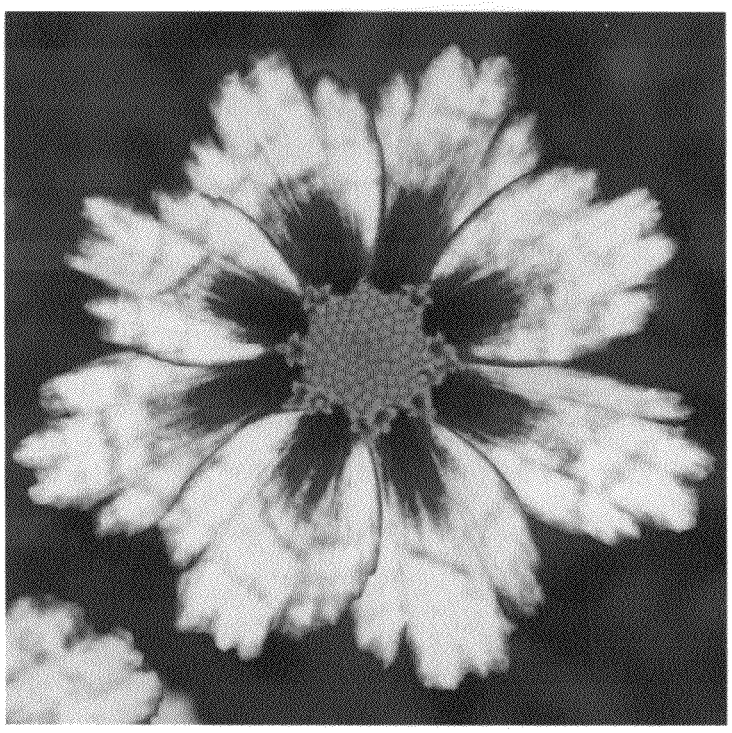

The photographs in FIG. 3 and FIG. 4 provide close-up views of the inflorescences of 'Star Cluster' under cool growing conditions. The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for two years in a test garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June until frost in central Massachusetts.

*Plant habit*.—Herbaceous perennial, clump-forming, densely branched, sturdy stems.

*Height and spread*.—Reaches 45 to 60 cm (18 to 24 inches in height) and 45 cm (18 inches) in spread after 3 months from a cutting.

*Cold hardiness*.—At least to U.S.D.A Zone 5.

*Diseases resistance*.—No particular resistance or susceptibility to diseases was observed.

*Root description*.—Fibrous, fine and well-branched.

Growth and propagation:

*Propagation*.—Terminal stem cuttings and division.

*Growth rate*.—Vigorous.

Stem description:

*Shape*.—Rounded, solid.

*Stem color*.—138A.

*Stem size*.—Main stem averages 30 cm in length and 3 mm in width with laterals variable in length and an average of 6 cm in length (excluding peduncles) and 2 mm in width.

*Stem surface*.—Glabrous.

*Branching habit*.—An average of 5 basal branches, each with 12 secondary branches, arising opposite at nodes, branch internode is variable but typically about 4 cm.

Foliage description:

*Leaf division*.—Simple.

*Leaf margins*.—Entire, finely ciliate towards base, cilia about 0.5 mm in length and 155C in color.

*Leaf size*.—Variable, an average of 4 cm in and 5 mm in width.

*Leaf shape*.—Linear.

*Leaf base*.—Cuneate.

*Leaf apex*.—Narrowly acute.

*Leaf venation*.—Pinnate, not prominent, 138A.

*Leaf attachment*.—Sessile.

*Leaf arrangement*.—Opposite.

*Leaf surface*.—Dull, glabrous.

*Leaf color*.—Young and mature upper surface; 138A, young and mature lower surface; 138B.

Flower description:

*Inflorescence type*.—Composite with double ray florets surrounding disk florets in the center, forming a radiant head, inflorescences are borne on branch terminals.

*Lastingness of inflorescence*.—About one week until senescence of ray flowers, bracts and disk flowers are persistent.

*Fragrance*.—None detected.

*Quantity of inflorescences*.—1 per lateral branch, an average of 37 per plant grown in a one-gallon container.

*Inflorescence size*.—An average of 1.2 cm in depth and up to 6.3 cm in diameter with disk portion an average of 8 mm in diameter.

*Inflorescence buds*.—Average of 8 mm in depth and 8 mm in diameter, shape is spherical, 160A in color surrounded by 8 bracts 138B in color.

*Peduncle*.—Strong, an average of 8.5 cm in length and 2 mm in diameter, 138A in color, glabrous surface.

Involucral bracts:

*Bract number*.—Two rows of 8.

*Bract arrangement*.—Outer bracts are un-fused and reflexed when flower is fully open and becoming horizontal after ray florets drop, inner bracts overlap and surround receptacle with a campanulate form with apical portion un-fused, spreading, and held close to lower surface of ray florets.

*Bract size*.—Outer bracts; up to 7 mm in length and 1.5 mm in width, inner bracts; up to 1.2 cm in length and 4 mm in width with free portion an average of 8 mm in length and 4 mm in width.

*Bract color*.—Outer bracts; 138B in both surfaces, inner bracts; 145A with apex and margin N144A.

*Bract texture*.—Glabrous on outer and inner bracts.

*Bract apex*.—Acute on outer and inner bracts.

*Bract base*.—Truncate on inner and outer bracts.

*Bract margins*.—Entire.

*Bract shape*.—Outer bracts; linear, inner bracts; broadly lanceolate.

Ray florets (sterile):

*Number*.—An average of 8 arranged primarily in one row.

*Shape*.—Broadly oblong with the appearance of three longitudinal sections with center section wider.

*Size*.—An average of 2.1 cm in length and 9 mm in width.

*Apex*.—Lobes emarginate.

*Base*.—Broadly cuneate.

*Margins*.—Entire on sides, notched at apex.

*Aspect*.—Held primarily horizontal.

*Texture*.—Glabrous on upper and lower surfaces.

*Color*.—Upper and lower surface when opening; 8C, upper and lower surface when mature; 155A with a spot of a color between N79B and N79C at the base (eyezone), under cooler temperature the eyezone becomes larger, the margins become N79 and the center of the petal becomes lightly suffused with 79C.

Disk flowers (perfect):

*Shape*.—Tubular, corolla is fused, flared at apex.

*Number*.—About 200.

*Size*.—About 6 mm in length and 2 mm in width.

*Color*.—En masse; 17A when fully open and becoming a blend of 17A and N144 when ray florets drop, corolla; base (tube) is 1C in color, flared portion is 17A and translucent.

*Receptacle*.—About 7 mm in diameter and 4 mm in depth, N144C in color.

Reproductive organs:

*Presence*.—Disk flowers are perfect, ray flowers are sterile.

*Gynoecium*.—1 Pistil, 6 mm in length, style is very fine and about 1C in color and translucent, bifid pilose stigma is 21B in color with branches about 1 mm in length and recurved, ovary is 1 mm in length, 0.5 mm in width, inferior, and 149D in color.

*Androcoecium*.—5 stamens, fused into tube surrounding style, 2 mm in length and 0.7 mm in width, about 165A in color, pollen abundant 17A in color.

*Fruit/seed*.—No fruit or seed development was observed.

It is claimed:

1. A new and distinct cultivar of *Coreopsis* plant named 'Star Cluster' as herein illustrated and described.

* * * * *